United States Patent [19]

Baasner et al.

[11] Patent Number: 4,764,611

[45] Date of Patent: Aug. 16, 1988

[54] PROCESS FOR THE SELECTIVE HYDROGENATION OF CHLORINE-CONTAINING PYRIMIDINES AND NEW PYRIMIDINES

[75] Inventors: Bernd Baasner, Leverkusen; Erich Klauke, Odenthal; Karl-Heinz Schündehütte, Leverkusen, all of Fed. Rep. of Germany

[73] Assignee: Bayer Aktiengesellschaft, Leverkusen, Fed. Rep. of Germany

[21] Appl. No.: 693,077

[22] Filed: Jan. 22, 1985

[30] Foreign Application Priority Data

Jan. 24, 1984 [DE] Fed. Rep. of Germany ....... 3402194

[51] Int. Cl.$^4$ ............................................ C07D 239/30
[52] U.S. Cl. ..................................... 544/334; 544/242
[58] Field of Search ............................... 544/334, 242

[56] References Cited

PUBLICATIONS

Henze et al., "J.A.C.S.", vol. 79(9), 1957, pp. 2230-2232.
Budesinsky et al., "Chemical Abstracts", vol. 63, 1965, Col. 18078h.
Feit et al., "Chemical Abstracts", vol. 81, 1974, Col. 120564f.
Harris et al., "Chemical Abstracts", vol. 88, 1978, Col. 88:22812k.
Rasmussen et al., "Chemical Abstracts", vol. 90, 1979, Col. 90:72140b.
Yamanaka et al., "Chemical Abstracts", vol. 92, 1980, Col. 92:94340k.
Schuendehuette et al., "Chemical Abstracts", vol. 94, 1981, Col. 94:141188v.
Klauke et al., "Chemical Abstracts", vol. 98, 1983, Col. 98:89312x.
Gershon et al., "Chemical Abstracts", vol. 98, 1983, Col. 98:198149v.
"Chemical Abstracts", vol. 72, 1970, Col. 90504f.
Busby et al., "Chemical Abstracts", vol. 92, 1980, Col. 92:128842t.
Brown, *The Pyrimidines, Supplement I*, 1970, Wiley-Interscience, New York, pp. 126-129.
Chemische Berichte, 110, Jahrgna No. 6, 1977, pp. 2106-2113, "Selektive Reduktion Einiger Halogen--Substituierter Pyridine der Vitamin B-6-Reihe[1]", Mladen Prostenik und Ivan Butula[2].
Journal of the Chemical Society, Section C, 1969, London, pp. 1866-1867, R. E. Banks et al, "Heterocyclic Polyfluoro-Compounds".
Australian Journal of Chemistry, vol. 21, 1968, Melbourne, pp. 243-255, D. J. Brown and T. C. Lee, Pyrimidine Reactions.
Journal of Fluorine Chemistry, vol. 21, 1982, Lausanne E. Klauke et al, "Fluorinated Heterocyclic Compounds: . . . ".

*Primary Examiner*—Glennon H. Hollrah
*Assistant Examiner*—James H. Turnipseed
*Attorney, Agent, or Firm*—Sprung Horn Kramer & Woods

[57] ABSTRACT

Chlorine-containing pyrimidines are selectively hydrogenated with elimination of hydrogen chloride, without other substituents and/or the aromatic ring being significantly attacked, by using a hydrogenation catalyst and a hydrogen chloride acceptor. This process gives predominantly new pyrimidines.

9 Claims, No Drawings

PROCESS FOR THE SELECTIVE HYDROGENATION OF CHLORINE-CONTAINING PYRIMIDINES AND NEW PYRIMIDINES

The present invention relates to a process for the selective hydrogenation of chlorine-containing pyrimidines, that is to say for replacing chlorine present in pyrimidines by hydrogen, without other substituents and/or the aromatic ring being significantly attacked. The present invention furthermore relates to new pyrimidines which are obtainable in this manner.

It is known that tetrafluoropyrimidine can be hydrogenated with lithium aluminum hydride in ether to give a mixture of 2,4,5-trifluoro- and 2,5-difluoropyrimidine (see J. Chem. Soc. (C), 1969, pages 1866–1867). In this process, however, the conversion is incomplete, and the two products are produced non-selectively, that is to say always as a mixture with one another. Moreover, the use of lithium aluminum hydride, which is difficult to handle, makes this process unsuitable for use on an industrial scale.

It is also known that 2,4,6-trichloro-5-methylpyrimidine can be reduced with zinc dust in benzene in the presence of concentrated ammonia solution (see Aust. J. Chem. 21, 243–245 (1968)). In this process, too, a mixture of several products is obtained.

A process for the selective hydrogenation of chlorine-containing pyrimidines has now been found, which is characterised in that chloropyrimidines of the formula (I)

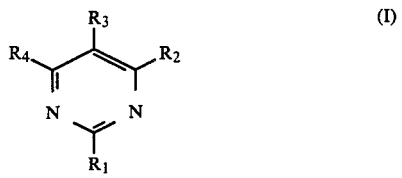

in which $R_1$, $R_2$, $R_3$ and $R_4$ are identical or different and represent fluorine, chlorine, hydrogen or $C_1$–$C_4$-alkyl groups, and some or all of the hydrogen atoms of the alkyl group or groups can optionally be replaced with fluorine and/or chlorine, and at least one of the radicals $R_2$ and $R_4$ only represents chlorine, are hydrogenated in the presence of a hydrogen chloride acceptor and of a hydrogenation catalyst.

Preferably used chloropyrimidines are those for which, in formula (I), $R_1$, $R_2$, $R_3$ and $R_4$ are identical or different and represent fluorine, chlorine, $CF_3$, $CF_2Cl$, $CCl_2F$, $CCl_3$, $CH_3$, $CHCl_2$, $CHF_2$ or $CH_2F$, $R_2$ and/or $R_4$ only representing chlorine.

Particularly preferred chloropyrimidines are those for which, in formula (I), $R_1$, $R_2$ and $R_3$ are identical or different and represent fluorine, chlorine or $CF_3$, and $R_4$ represents fluorine or chlorine, $R_4$ only representing fluorine when $R_2$ represents chlorine.

The chloropyrimidines to be employed are readily available. They are either known, or can be prepared analogously to the known chloropyrimidines, for example by partial fluorination of chlorine-containing pyrimidines (see J. Fluorine Chem. 21, 495–513 (1982)), or by selective rechlorination of fluorine-containing pyrimidines (see German Offenlegungsschrift No. 3,328,154).

The process according to the invention is carried out in the presence of a hydrogen chloride acceptor. Examples of such hydrogen chloride acceptors are tertiary amines and basis inorganic compounds. The tertiary amines must not contain any reactive hydrogen atoms, since these may react in an undesirable manner with halogen atoms on the pyrimidine ring to form amines of pyrimidine. Preferred tertiary amines are $C_1$–$C_4$-alkylamines and pyridine, and preferred basic inorganic compounds are barium oxide, calcium carbonate, sodium carbonate and potassium carbonate. Triethylamine is particularly preferably employed.

The hydrogen chloride acceptor is preferably employed in a stoichiometric amount or in slight excess, for example in an excess of up to 10 mol %, relative to the stoichiometric amount. The stoichiometric amount is particularly preferably employed.

If the chloropyrimidine employed has more than one chlorine atom which can be split off by hydrogenation, these chlorine atoms are split off selectively in succession. The number of chlorine atoms to be split off can be influenced by the amount of hydrogen chloride acceptor employed. If, in the process according to the invention, for example a chloropyrimidine having two chlorine atoms which can be split off by hydrogenation, and one mol of a hydrogen chloride acceptor is employed per mol of such a chloropyrimidine, only one chlorine atom is split off selectively. If, in this case, two mol of a hydrogen chloride acceptor are employed per mol of chloropyrimidine, both chlorine atoms are split off selectively.

The process according to the invention is carried out in the presence of hydrogenation catalysts. Examples of suitable hydrogenation catalysts are those which consist of metals and/or compounds of elements of sub-group eight of Mendeleev's periodic table of the elements, or contain these. In this context, the metals ruthenium, rhodium, palladium, platinum and nickel and their compounds are preferred. The metal compounds can be, for example, oxides, hydroxides and/or oxide hydrates. Furthermore, the metals copper, vanadium, molybdenum, chromium and/or manganese and compounds of these metals can be present.

The hydrogenation catalysts can consist exclusively or predominantly of hydrogen-transferring substances, but these may also be applied on carrier materials. Examples of suitable carrier materials for the hydrogen-transferring substances are: inorganic materials, such as kieselguhr, silica, aluminum oxides, alkali metal and alkaline earth metal silicates, aluminum silicates, montmorillonite, zeolites, spinels, dolomite, kaolin, magnesium silicates, zirconium oxide, zinc oxide, calcium carbonate, silicon carbide, aluminum phosphate, boron phosphate, asbestos, active carbon or barium sulphate, but also organic materials, for example naturally occurring or synthetic compounds having high molecular weights, such as silk, polyamides, polystyrenes, cellulose or polyurethanes. Inorganic carrier materials are preferred. The carrier material can be, for example, in the form of spheres, extrudates, filaments, cylinders or polygons or in powder form.

Supported catalysts of this type can contain in general 0.5 to 50% by weight, preferably 1 to 10% by weight, of hydrogen-transferring substance, relative to the total weight of the supported catalyst. The hydrogen-transferring substance can be distributed homogeneously in the carrier material, but preferred catalysts are those where the hydrogen-transferring substance is deposited in the outer layer of the catalysts or on their surface. The preparation and the shaping of catalysts which can be used in the process according to the invention can be carried out in a known manner (see, for example, Houben-Weyl, Methoden der organischen Chemie [Methods of organic Chemistry], Volume IV, 1c, Part I, pages 16–26, Georg Thieme Verlag, Stuttgart 1980).

Preferred supporting catalysts are ruthenium on carbon, ruthenium on aluminum oxide, rhodium on carbon, rhodium or aluminum oxide, palladium on carbon, palladium on aluminum oxide, palladium on calcium carbonate, palladium on barium sulphate, palladium on silica, platinum on carbon and platinum on aluminum oxide.

Preferred hydrogenation catalysts which consist exclusively or predominantly of hydrogen-transferring substance are, for example, oxide catalysts, such as palladium oxide, platinum oxide, ruthenium oxide and/or rhodium oxide/platinum oxide according to Nishimura, as well as black catalysts, such as palladium black, platinum black or rhodium black, which can be prepared by reduction of the corresponding metal salts or metal salt mixtures with, for example, hydrazine, formaldehyde, hydrogen or more electropositive metals.

Particularly preferred catalysts for the process according to the invention are palladium on carbon, palladium on aluminum oxide, palladium on silica and palladium on calcium carbonate.

It is also possible to use skeleton catalysts of the Raney type, Raney nickel being preferred.

In the process according to the invention, the hydrogenation catalyst can be employed, for example, in an amount such that 0.05 to 2.5% by weight, relative to the total weight of the reaction mixture, of hydrogen-transferring substance is present. The amount is preferably 0.1 to 1% by weight.

In carrying out the process according to the invention, it is also possible to use mixtures of two or more of the stated hydrogenation catalysts.

The catalytic activity of the hydrogenation catalysts is in general substantially retained when the process according to the invention is carried out, so that these catalysts can be used repeatedly in a discontinuous procedure and can be employed for a relatively long time in a continuous procedure.

In general, it is advantageous to carry out the process according to the invention in the presence of a solvent.

Examples of suitable solvents are inert organic solvents. Suitable examples are alcohols, such as methanol, ethanol, ethylene glycol and diethylene glycol, ethers, such as dioxane, tetrahydrofuran, ethylene glycol monomethyl ether, ethylene glycol monoethyl ether, ethylene glycol dimethyl ether, diethylene glycol monomethyl ether and diethylene glycol dimethyl ether, saturated hydrocarbons, such as cyclohexane, or esters, such as ethyl acetate. Because of their solvent properties and their low boiling points, methanol, ethanol and ethyl acetate are particularly preferred solvents.

The process according to the invention can be carried out in reaction apparatuses which are suitable for hydrogenation under pressure. Suitable materials for the reaction apparatuses are, for example, glass, enamel, steel or stainless steel.

The hydrogen pressure under which the hydrogenation is carried out can be, for example in the range from 1.2 to 25 bar. The hydrogen pressure is preferably from 1.5 to 15 bar, particularly preferably from 2 to 10 bar.

The reaction temperature can be, for example, between 20° and 100° C., temperatures between 20° and 90° C. are preferred, and those between 30° and 80° C. are particularly preferred.

The reaction time required for the process according to the invention depends on the reaction rate, on the hydrogen partial pressure, on the thoroughness with which the reaction mixture is mixed, and on the activity and concentration of the hydrogenation catalyst. In general, the required reaction time is in the range from 15 minutes to several hours.

For example, in the simplest embodiment, the process according to the invention can be carried out discontinuously, in the following manner: an autoclave which is provided with a stirring or mixing unit and which can be thermostated is charged, in a suitable manner, with chloropyrimidine to be hydrogenated, the hydrogenation catalyst, a solvent and a hydrogen chloride acceptor. Thereafter, hydrogen is forced in until the desired pressure is reached, and the mixture is heated to the chosen reaction temperature while mixing thoroughly. The course of the reaction can be readily monitored by measuring the amount of hydrogen consumed, which is compensated by feeding in further hydrogen. The hydrogenation is complete when hydrogen is no longer consumed, and the amount of hydrogen consumed corresponds approximately to the theoretically required amount of hydrogen.

The mixture present after the hydrogenation can be worked up, for example, as follows: when the hydrogenation is complete, the reaction vessel is cooled, the pressure is let down and the solid amine hydrochloride, or the inorganic salts present, and the catalyst are filtered off and rinsed with the solvent used, and the solvent is then removed under reduced pressure or under atmospheric pressure. The crude product which remains can likewise be purified further by distillation under reduced pressure or under atmospheric pressure or, in the case of crystalline crude product, by recrystallization. When high-boiling solvents are used, it is also possible first to distil off the hydrogenated pyrimidine derivative.

The products obtainable with the process according to the invention, some of which are known, but the bulk of which are new, of the formula (II)

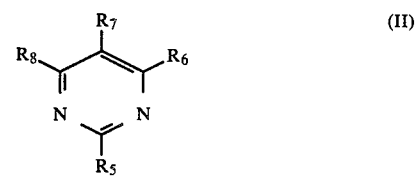

in which $R_5$, $R_6$, $R_7$ and $R_8$ are identical or different and represent fluorine, chlorine, hydrogen or $C_1$–$C_4$-alkyl groups, and some or all of the hydrogen atoms of the alkyl group or groups can optionally be replaced with fluorine and/or chlorine, and at least one of the radicals $R_6$ and $R_8$ represents hydrogen, are, as such, intermediate products for herbicides, growth regulators and pharmaceuticals, or give such intermediates after further reaction.

For example, products of the formula (II), in which $R_5$ and $R_8$ are identical or different and represent fluorine and/or chlorine, $R_6$ represents hydrogen and $R_7$ has the meaning given above, can be converted by alkaline or acidic hydrolysis to the corresponding pyrimidine diones (uracils), which are herbicides or are useful as intermediate products for the preparation of herbicides and growth regulators.

The hydrolysis can be effected using an acid or alkali such as sulfuric acid, hydrochloric acid, acetic acid, nitric acid, phosphoric acid, sodium hydroxide or potassium hydroxide. Hydrolysis is performed using generally at least 2 moles of water and 2 moles alkali or acid per mole of starting material and the hydrolysis is effected at a temperature from 0° to 160° C. Generally, when an acid is in employed for the hydrolysis the same is employed in a 5 to 95% strength. When an alkali is used a 3 to 50% strength aqueous solution thereof is utilized.

For example, 5-fluoro-2,4(1H,3H)-pyrimidinedione (=5-fluorouracil) is obtainable in this manner, this compound being a known carcinostatic and also being used as a starting material for the synthesis of nucleoside derivatives which inhibit tumour growth (see, for example, Biomedical Aspects of Fluorine Chemistry, Edited by R. Filler and Y. Kobayaski, Kodanska Ltd. Tokyo, and Elsevier Biomedical Press Amsterdam-New York-Oxford (1982), and the literature cited therein).

The present invention furthermore relates to new pyrimidines of the formula (III)

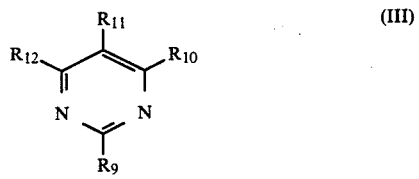

in which $R_9$, $R_{10}$, $R_{11}$ and $R_{12}$ are identical or different and represent fluorine, chlorine, hydrogen or $C_1$–$C_4$-alkyl groups, and some or all of the hydrogen atoms of the alkyl group or groups can optionally be replaced by fluorine and/or chlorine, and at least one of the radicals $R_{10}$ and $R_{12}$ represents hydrogen, and the combinations $R_9$ and $R_{11}=F$, $R_{10}$ and $R_{12}=H$, $R_9=Cl$, $R_{10}$ and $R_{12}=H$, $R_{11}=F$, $R_9$ and $R_{12}=Cl$, $R_{10}=H$, $R_{11}=F$ and $R_9$, $R_{11}$ and $R_{12}=F$ and $R_{10}=H$ are excluded.

Preferred pyrimidines of the formula (III) are those in which $R_9$, $R_{10}$, $R_{11}$ and $R_{12}$ are identical or different and represent fluorine, chlorine, hydrogen, $CF_3$, $CF_2Cl$, $CFCl_2$, $CCl_3$, $CH_3$, $CHCl_2$, $CHF_2$ or $CH_2F$, and $R_{10}$ and/or $R_{12}$ represent hydrogen, and the combinations of the radicals $R_9$ to $R_{12}$ excluded in the general explanation of the formula (III) are also excluded here.

Other preferred pyrimidines of the formula (III) are those in which $R_9$ and $R_{10}$ are identical or different and represent fluorine, chlorine, hydrogen, methyl or a methyl group which is substituted as desired by fluorine and/or chlorine, $R_{11}$ represents fluorine and $R_{12}$ represents hydrogen, and the combinations of the radicals $R_9$ to $R_{12}$ excluded in the general explanation of the formula (III) are also excluded here.

Further preferred pyrimidines of the formula (III) are those in which $R_9$ and $R_{11}$ are identical or different and represent fluorine, chlorine, hydrogen, methyl or a methyl group which is substituted as desired by fluorine and/or chlorine, $R_{10}$ represent hydrogen or fluorine and $R_{12}$ represents hydrogen, and the combinations of the radicals $R_9$ to $R_{12}$ excluded in the general explanation of the formula (III) are also excluded here.

Particularly preferred pyrimidines of the formula (III) are those in which $R_9$ represents fluorine, chlorine, hydrogen, methyl or a methyl group which is substituted as desired by fluorine and/or chlorine, $R_{10}$ represents hydrogen, $R_{11}$ represents fluorine and $R_{12}$ represents hydrogen, fluorine or chlorine, and the combinations of the radicals $R_9$ to $R_{12}$ excluded in the general explanation of the formula (III) are also excluded here.

Further particularly preferred pyrimidines of the formula (III) are those in which $R_{10}$ represents fluorine, chlorine, hydrogen, methyl or a methyl group which is substituted as desired by fluorine and/or chlorine, $R_9$ represents fluorine or chlorine, $R_{11}$ represents fluorine and $R_{12}$ represents hydrogen, and the combinations of the radicals $R_9$ to $R_{12}$ excluded in the general explanation of the formula (III) are also excluded here.

Further particularly preferred pyrimidines of the formula (III) are those in which $R_{11}$ represents fluorine, chlorine, hydrogen, methyl or a methyl group which is substituted as desired by fluorine and/or chlorine, $R_{10}$ represents hydrogen, $R_9$ represents fluorine or chlorine and $R_{12}$ represents hydrogen, fluorine or chlorine, and the combinations of the radicals $R_9$ to $R_{12}$ excluded in the general explanation of the formula (III) are also excluded here.

A very particularly preferred pyrimidine of the formula (III) is that in which $R_9$ and $R_{11}$ represent fluorine, $R_{10}$ represents hydrogen and $R_{12}$ represents chlorine.

The preparation and the use of the new pyrimidines of the formula (III) have already been described above.

It is extremely surprising that, using the process according to the invention, pyrimidines which hitherto were obtainable only by a very inconvenient method can be prepared in a simple manner and in good yields. It is also surprising that the process according to the invention gives new pyrimidines which are valuable intermediate products. It was in no way to be expected that the hydrogenation according to the invention would be successful, since both the pyrimidine nucleus and substituents bonded to the pyrimidine nucleus, in particular further fluorine and/or chlorine atoms, are available for hydrogenation; unexpectedly, however, they are not attacked.

The examples which follow illustrate the process according to the invention and the new pyrimidines according to the invention, without restricting the present invention to these.

EXAMPLES

Example 1

185 g (1 mol) of 2,5-difluoro-4,6-dichloropyrimidine in 1800 ml of ethyl acetate were hydrogenated in a stirred stainless steel autoclave for 95 minutes at 30° C. and under a hydrogen pressure of 3.5 bar, with the addition of 110 g of triethylamine and 15 g of palladium on carbon (5% strength by weight). Thereafter, the solid components of the reaction mixture were filtered off, the residue was washed with ethyl acetate, and the wash liquid together with the filtrate was distilled under atmospheric pressure over a 30 cm packed column. After the solvent had been distilled off, 106 g of 2,5-difluoro-4-chloropyrimidine having a boiling point of 145° to 146° C. were obtained. The yield was accordingly 70.5% of theory. According to analysis by gas chromatography, the reaction product isolated had a purity of 94.7%.

EXAMPLES 2 to 10

The procedure described in Example 1 was followed, except that other starting materials were employed. The starting materials, the reaction products and other data are given in Table 1.

TABLE 1

| Example | Starting material (pyrimidine) | Reaction product (pyrimidine) | Yield (% of theory) | Boiling point (°C./mbar) | Purity (%) |
|---|---|---|---|---|---|
| 2 | 2,4,6-trichloro-5-fluoro- | 2,4-dichloro-5-fluoro- | 68 | 88–91/30 | 94.1 |
| 3 | 2,4,5-trifluoro-6-chloro- | 2,4,5-trifluoro- | 87 | 92–93/1013 | 98.4 |
| 4 | 2,5-difluoro-4-chloro-6-trifluoromethyl- | 2,5-difluoro-6-trifluoromethyl- | 88 | 115–116/1013 | 96.6 |
| 5 | 2,4-dichloro-5-fluoro-6-trifluoromethyl | 2-chloro-5-fluoro-6-trifluoromethyl- | 75 | 138–140/300 | 93.1 |
| 6 | 2-trifluoromethyl-4-chloro-5,6-difluoro- | 2-trifluoromethyl-5,6-difluoro- | 86.6 | 113–114/1013 | 95.2 |
| 7 | 2-trifluoromethyl-4,6-dichloro-5-fluoro- | 2-trifluoromethyl-4-chloro-5-fluoro- | 95.5 | 123–125/1013 | 98.6 |
| 8 | 2-chlorodifluoromethyl-4,5-dichloro-6-fluoro | 2-chlorodifluoromethyl-5-chloro-6-fluoro- | 73 | 34–35/80 | 97.0 |
| 9 | 2-methyl-5,6-dichloro-4-fluoro- | 2-methyl-5-chloro-4-fluoro- | 76 | * | 96.8 |
| 10 | 2-fluoro-4,5-dichloro-6-methyl- | 2-fluoro-5-chloro-6-methyl- | 93 | 58–60/20 | 95.7 |

* Melting point 220–222° C.; isolated by filtration and recrystallisation from ethyl acetate

Example 11

50 g (0.27 mol) of 2,5-difluoro-4,6-dichloropyrimidine in 500 ml of ethyl acetate were hydrogenated in a glass apparatus for 3.5 hours at 50° C. and under a hydrogen pressure of 4 bar, with the addition of 60 g of triethylamine and 7 g of palladium on carbon (5% strength by weight). Thereafter, the solid components of the reaction mixture were filtered off, the residue was washed with ethyl acetate, and the wash liquid together with the filtrate was distilled under atmospheric pressure through a 30 cm packed column. After the solvent had been distilled off, 25.7 g of 2,5-difluoropyrimidine having a boiling point of 116° to 117° C. were obtained. The yield was accordingly 82.2% of theory. According to analysis by gas chromatography, the product isolated had a purity of 98.3%.

Examples 12 to 14

The procedure described in Example 11 was followed, except that other starting materials were employed. The starting materials, and reaction products and other data are given in Table 2.

TABLE

| Example | Starting material (pyrimidine) | Reaction product (pyrimidine) | Yield (% of theory) | Boiling point (°C./mbar) | Purity % |
|---|---|---|---|---|---|
| 12 | 2,4,6-trichloro-5-fluoro- | 2-chloro-5-fluoro- | 78 | 92–94/100 | 96.9 |
| 13 | 2-trifluoromethyl-4,6-dichloro-5-fluoro- | 2-trifluoromethyl-5-fluoro- | 92 | 130–132/1013 | 99.6 |
| 14 | 2-trichloromethyl-4,6-dichloro-5-fluoro- | 2-trichloromethyl-5-fluoro- | 63 | 120–122/30 | 92.7 |

The reaction products from Examples 12 to 14 were additionally characterised by means of $^{19}$F— and $^{1}$H— NMR spectroscopy, and using a mass spectrometer.

Example 15 (not according to the invention)

150.5 g (1 mol) of the 2,5-difluoro-4-chloropyrimidine obtained according to Example 1 were taken up in 1.5 l of water, and the stirred solution was heated to 80° C. (internal temperature). The dropwise addition of 200 g of 45% strength by weight aqueous sodium hydroxide solution was started during the heating-up procedure. When the addition was complete, stirring was continued for 4 hours at 80° C. After the mixture had cooled, it was neutralised with concentrated hydrochloric acid, and the precipitated solid was filtered off under suction. This solid was digested with 500 ml of water, once again filtered off under suction and dried at 50° C. in vacuo until it was anhydrous. 121 g (93% of theory) of 5-fluoro-2,4-(1H,3H)-pyrimidinedione (=5-fluorouracil) having a melting point of 280° to 282° C. (decomposition) were obtained.

What is claimed is:

1. A process for the selective hydrogenation of a chlorine-containing pyrimidine which comprises contacting a chloropyrimidine of the formula

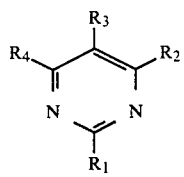

in which
R$_1$, R$_2$, R$_3$ and R$_4$ are identical or different and represent fluorine, chlorine, hydrogen or C$_1$ to C$_4$-alkyl groups with some of all of the hydrogen atoms of the alkyl group or groups being optionally replaceable with fluorine and/or chlorine, at least one of the radicals R$_2$ and R$_4$ representing only chlorine and at least one of R$_1$, R$_2$, R$_3$ or R$_4$ is fluorine,
with hydrogen in the presence of a hydrogen chloride acceptor and a hydrogenation catalyst.

2. A process according to claim 1 wherein said chloropyrimidine is one in which R$_1$, R$_2$, R$_3$ and R$_4$ are identical or different and represent fluorine, chlorine, CF$_3$, CF$_2$Cl, CCl$_2$F, CCl$_3$, CH$_3$, CHCl$_2$, CHF$_2$ or CH$_2$F, and R$_2$ and/or R$_4$ only represent chlorine.

3. A process according to claim 1 wherein said chloropyrimidine is one in which R$_1$, R$_2$ and R$_3$ are identical or different and represent fluorine, chlorine or CF$_3$, and R$_4$ represents fluorine or chlorine, R$_4$ representing fluorine only when R$_2$ represents chlorine.

4. A process according to claim 1 wherein the hydrogenation is carried out in the presence of a tertiary amine or a basic inorganic compound.

5. A process according to claim 1 wherein the process is carried out in the presence of a hydrogenation catalyst comprising a metal and/or compound of an element of sub-group 8 of the Medeleev periodic table of elements.

6. A process according to claim 1 wherein the process is carried out under a hydrogen pressure from 1.2 to 25 bar at a reaction temperature of between 20° and 100° C.

7. A pyrimidine of the formula

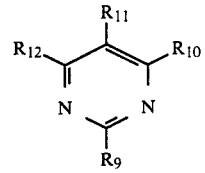

in which
R$_9$, R$_{10}$ and R$_{12}$ are identical or different and represent fluorine, chlorine, hydrogen or C$_1$–C$_4$-alkyl groups, and some or all of the hydrogen atoms of the alkyl group or groups can optionally be replaced by fluorine and/or chlorine, at least one of the radicals R$_{10}$ and R$_{12}$ represents hydrogen,
R$_{11}$ represents fluorine, pyrimidines wherein R$_9$ and R$_{11}$=F, R$_{10}$ and R$_{12}$=H, R$_9$=Cl, R$_{10}$ and R$_{12}$=H, R$_{11}$=F, R$_9$ and R$_{12}$=Cl, R$_{10}$=H, R$_{11}$=F and R$_9$, R$_{11}$ and R$_{12}$=F and R$_{10}$=H are excluded.

8. A pyrimidine according to claim 7 wherein R$_9$, R$_{10}$ and R$_{12}$ are identical or different and represent fluorine, chlorine, hydrogen, CF$_3$, CF$_2$Cl, CFCl$_2$, CCl$_3$, CH$_3$, CHCl$_2$, CHF$_2$ or CH$_2$F, and R$_{10}$ and/or R$_{12}$ represent hydrogen.

9. A pyrimidine according to claim 7 wherein R$_9$ and R$_{11}$ represent fluorine, R$_{10}$ represents hydrogen and R$_{12}$ represents chlorine.

* * * * *